United States Patent [19]
Roos

[11] Patent Number: 4,578,575
[45] Date of Patent: Mar. 25, 1986

[54] OPERATING THEATRE LAMP

[75] Inventor: Eberhard Roos, Tuttlingen, Fed. Rep. of Germany

[73] Assignee: Delma, electro- und medizinische Appatebau Gesellschaft mbH, Tuttlingen, Fed. Rep. of Germany

[21] Appl. No.: 552,647

[22] Filed: Nov. 17, 1983

[30] Foreign Application Priority Data

Nov. 25, 1982 [DE] Fed. Rep. of Germany ....... 3243710

[51] Int. Cl.$^4$ ............................................. G01J 1/20
[52] U.S. Cl. ................ 250/203 R; 362/286; 362/804
[58] Field of Search ................ 250/203 R, 221, 222.1, 250/234; 362/804, 269, 272, 275, 285, 286, 287; 356/141, 152

[56] References Cited

U.S. PATENT DOCUMENTS 3,603,686 9/1971 Paine et al. .................... 250/203 R Primary Examiner—Edward P. Westin
Attorney, Agent, or Firm—Townsend and Townsend

[57] ABSTRACT

An operating theatre lamp which transmits a directed beam of light is pivotally arranged about two axes (43, 44), which are substantially perpendicular to one another and to the beam of light (12), above the site of an operation 13. The pivotal movement of the operating theatre lamp is effected by two positioning motors (41, 42). The operating theatre lamp has a light beam selector (11) which cooperates with a control reflector (38) and a control circuit (40) in such a way that the lamp reflector (55) of the operating theatre lamp automatically follows the control reflector during displacement of the control reflector (38) within the site of the operation.

9 Claims, 4 Drawing Figures

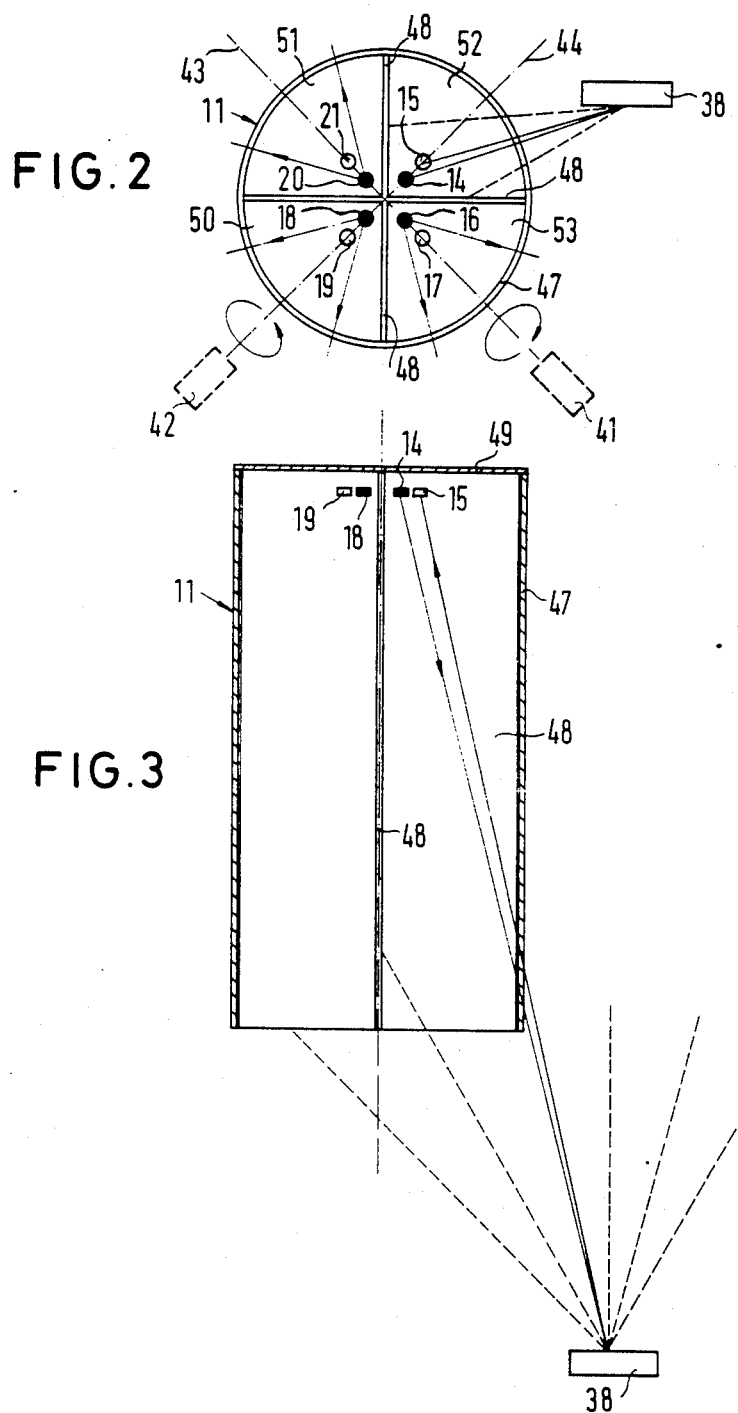

OPERATING THEATRE LAMP

BACKGROUND OF THE INVENTION

1. Field of the Invention

The invention relates to an operating theatre lamp which transmits a directed beam of light, which is pivotally arranged about two axes which are substantially perpendicular to one another and to the light beam above the site of an operation, and which generates a restricted field of light within the site of the operation, wherein said restricted field of light can be substantially horizontally displaced through pivotal movement of the lamp.

2. Description of Related Art

In operating theatre lamps of known construction either one large light reflector or several small light reflectors are built into the lamp in such a way that the light beam or beams emerging from the reflector/reflectors illuminate, at 1 m distance, a round field of approximately 18 to 22 cm diameter with maximum light intensity. The adjustment of the field of light generated by the operating theatre lamp to coincide with the site of the operation, which is to be as brightly illuminated as possible, is effected either by the surgeon himself, by means of a sterilisable handle mounted on the body of the lamp, or by an assistent on an instruction from the surgeon. Both ways of adjusting the field of light are problematic. The sterility of a handle mounted on the lamp body is not always reliably ensured, and the danger that the surgeon or assistant will bang his head against this handle is large. Moreover, in order to grasp the handle, the surgeon must look upwardly, and thus into the light beams, and is thus dazzled. The use of sterilisable handles for adjusting the field of light is thus decried by many surgeons. The precise adjustment of the field of light by an unsterile person is likewise difficult for a variety of reasons, and is in many cases simply impossible. For one thing the adjustment of the field of light by appropriate adjustment of the lamp is often problematic because unsterile assistants must maintain a certain minimum distance from the surgical team who are wearing sterile clothing and, particularly can often only reach the body of the lamp with their hands with difficulty, particulary if of small stature. Furthermore, having regard to the distance which the assistant must remain from the surgeon's team, from the patient who is covered with sterile coverings and from the instrument table with the sterile instruments which are placed thereon, it is often impossible for the assistant to see the actual site of the operation directly, if at all, and thus the adjustment of the field of light is only possible in response to commands by the surgeon.

The object underlying the invention is thus to provide an operating theatre lamp of the initially named kind which can be ideally adjusted to the desired area within the site of the operation by the operator himself or by a person belonging to the surgeon's team without contact with the lamp and solely by contact with a readily sterilisable article.

SUMMARY OF THE INVENTION

In order to satisfy this object the invention provides that the operating theatre lamp has a light beam selector, which is movable with the lamp, which comprises light sources and light receivers, and which concentrates a beam of electromagnetic radiation, narrower than said light beam and in a different frequency range into a control field within the field of light; in that a control reflector is provided which is displaceable in a horizontal plane within the site of the operation, which is matched to the size of the control field and is likewise smaller than the field of light and which reflects the electromagnetic radiation back on itself, at least in part, to the photoreceivers; and in that the light sources and the photoreceivers are so arranged in the light beam selector that, when the control reflectors leaves the control field, the photoreceivers transmit signals to an electronic control circuit through which positioning motors connected to the control circuit are actuated to pivot the lamp about the two axes in the sense of a follow-up adjustment of the control field.

The invention thus provides a remote control for an operating theatre lamp which makes it possible for the surgeon to so align the light beam from the operating theatre lamp, without the aid of persons outside of the surgeon's team and with the aid of a control reflector which can be readily sterilised, that the illumination and visibility conditions which he requires at the operating site are present. As the control reflector can readily be constructed as a structure which is insensitive to the heat used for sterilisation, and can also be comfortably and easily handled, there are no problems in providing a perfectly sterilised control reflector for each new operation. In view of the constructional simplicity, and thus low cost, of the control reflector it is readily possible to hold several sterilised control reflectors for a operating theatre lamp at the ready and these can then be used as required. The control reflector in accordance with the invention thus belongs, to a certain degree, to the operating instruments. It is particularly advantageous that the control reflector itself does not need to be displaceably mounted in any way but can instead be freely held and displaced by the surgeon. As soon as the control reflector leaves the control field during this horizontal movement the control field, and thus the field of light, will be automatically controlled to follow the movement of the control reflector.

In order to ensure ideal centering of the field of light in the desired region of the site of the operation the control field should be arranged at the center of the field of light. In order to provide a control reflector which, on the one hand, is simple to handle and not too large and, on the other hand, in order to ensure a good centering of the light beam in the desired area, it is expedient for the diameter of the control field to amount to from $\frac{1}{4}$ to $\frac{3}{4}$ and in particular to approximately $\frac{1}{2}$ of the diameter of the field of light.

It is particularly advantageous for the control reflector to be a retroreflector, in particular a triple prism. In this case it is sufficient for the reflecting surface of the control reflector to be only approximately aligned in the direction of the operating theatre lamp because the beams of the particular electromagnetic radiation which fall on the control reflector from the operating theatre lamp are reflected back on themselves to the light beam selector. The surgeon does not therefore need to be particularly attentive to the alignment of the control reflector with the light beam selector when handling the control reflector of the invention.

A particularly advantageous embodiment is characterised in that the light sources and photoreceivers are distributed pairwise in four sectors, the bisectors of which extend substantially parallel to the said axes; wherein the photoreceivers which are arranged on a bisector, receive light which does not fall centrally into the light beam selector with idfferential intensity and control, via the control circuit, the pivoting of the lamp about the axes which are at right angles to the relevant bisectors. The angular selection is in this arrangement preferably obtained by arranging the light sources and photoreceivers at the base of a tube which is open at the bottom and which has two flat internal walls arranged perpendicular to one another in accordance with the sectors.

In order to clearly associate the individual pairs of light sources and photoreceivers with one another and to decouple them from the remaining pairs a further embodiment provides that each light source is operated with a different pulse frequency, and that the associated photoreceivers are tuned by means of electric filters provided within the control circuit to the pulse frequency of the associated light source. In this manner signals received from non-associated light sources have no influence on the positioning motor controlled by the relevant photoreceiver.

The particular electromagnetic radiation is expediently an infrared radiation, whereby an overlap with the frequency range of the operational light beam can be effectively avoided.

BRIEF DESCRIPTION OF THE DRAWING

The invention will now be described by way of example only in the following and with reference to the drawings which show.

DESCRIPTION OF THE PREFERRED EMBODIMENT

Figure 1:
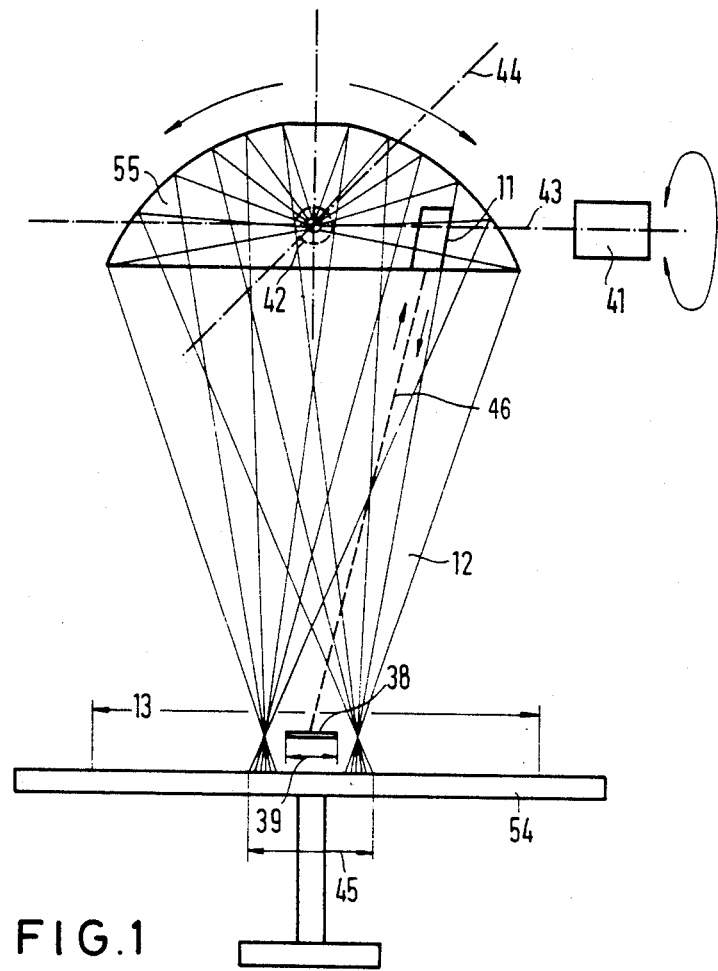
FIG. 1 a schematic side view of an operating theatre lamp with an operating table arranged therebelow, FIG. 2 a view, as seen from below, of a light beam selector (11) used with the operating theatre lamp of FIG. 1, FIG. 3 a schematic partly sectioned side view of the light beam selector (11) of FIG. 2 as seen in the direction of one of the flat intermediate walls 48, and FIG. 4 a schematic block circuit diagram of the operating theatre lamp with the attached electronic control circuit 40.

As seen in FIG. 1 a narrowly bundled infrared beam 46 is radiated from a light beam selector 11 which is built into the lamp reflector 55 of the operating theatre lamp, which is pivotable about the mutually perpendicular horizontal axes 43, 44, substantially parallel to the light beam 12 emerging from the lamp reflector 55, and is reflected back into the light beam selector 11 by a control reflector 38 in the form of a triple prism held by an operator in the field of light 39 located within the site of the operation 13 above the operating table 54.

The infrared radiation illuminates solely a control field 39 of narrower construction than the field of light 45, with the size of the control field 39 corresponding essentially to the area of the control reflector 38.

The light beam selector 11 is illustrated in detail in FIGS. 2 and 3. A light-cylindrical tube 47 which is open at the bottom, is subdivided throughout its entire length up to an upper cover 49 into four equal sectors 50, 51, 52, 53 by two flat intermediate or partition walls 48 which are arranged at an angle of 90° to one another. One each of a diode formed by an infrared light source 14, 16, 18 and 20 and one each of an infrared photoreceiver 15, 17, 19 and 21 also formed by a diode are arranged pairwise for each sector on the cove 49 at an angle of 45° to the intermediate walls 48. The intermediate walls 48 are in turn inclined at 45° to the axes 43, 44 of the lamp reflector 55 illustrated in FIG. 1

In the arrangement of FIG. 3 the control reflector 38 is initially only able to reflect the light radiated from the light source 14 back on itself to the photoreceiver 15. The light beams from the light sources 16, 18 and 20 are intercepted by the intermediate walls 48 and shielded in this way from the control reflector 38. The photoreceivers 17, 19 and 21 do not therefore receive any reflected signals from the control reflector 38.

As seen in FIGS. 2 and 3 the pivoting of the lamp reflector 55 about the two mutually perpendical horizontal axes 43, 44 is effected by two schematically illustrated positioning motors 41, 42. The positioning motors 41, 42 are driven by an electronic control circuit 40 shown in FIG. 4 from the signals of the photoreceivers 15, 19, 17, 21. The four sectors 50, 51, 52, 53 are once again schematically illustrated in FIG. 4. A respective transmitter 22, 23, 24 and 25 which energises the light sources 14, 18, 16, 20 is associated with each sector. The transmitters 22, 23, 24 and 25 are connected to a power supply 57 within the control circuit 40.

Each transmitter operates with its own pulse frequency and energises the associated light source 14, 18, 16 or 20 with light chopped in accordance with this pulse frequency. The infrared radiation 46 from the light sources passes in the manner illustrated schematically in FIG. 4 to the control reflector 38. The control reflector reflects the incident light, depending on its horizontall position relative to the control field 39 (FIG. 1) more or less to the photoreceivers 15, 17, 19, 21. These photoreceivers are connected to preamplifiers 26, 27, 28, 29 which are in each case followed by a decoder 30, 31, 32, 33. The decoders are connected in the manner which can be seen from FIG. 4 with one another and with two logic circuits 34, 35 to which the motor control circuits 36, 37 are connected which are in turn connected to the positioning motors 41, 42. All the described circuit elements are supplied with voltage or power by the power supply 57.

Figure 4:
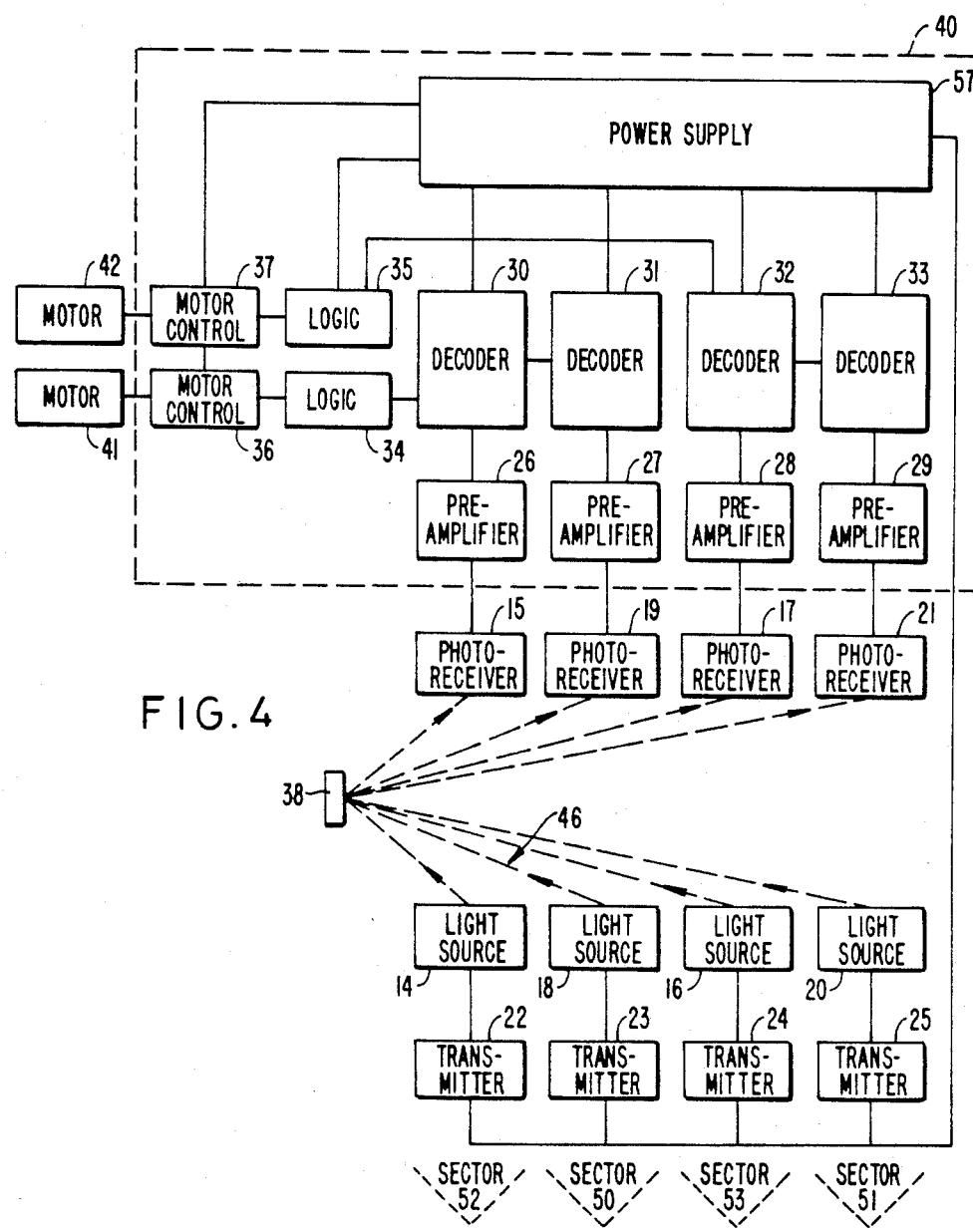

As seen in FIG. 4 the transmitters 22, 23, 24, 25 thus deliver a permanently repeating signal in two phase code to the light sources 14, 16, 18, 20, in each case with a different frequency. The light sources transmit a corresponding infrared signal. The preamplifiers 26, 27, 28 and 29 amplify the signal recorded by the photoreceivers 15, 17, 19, 21 by about 60 db. The decoders 30, 31, 32, 33 filter out the signal that they are to process, i.e. the signal frequency associated with the sectors 50, 51, 52 and 53 illustrated in FIGS. 2 and 3, and decide on the circuit state L or H. If, for example, the signal radiated from the light source 14 arranged in the sector 52 of the light beam selector 11 is reflected from the control reflector 38 to the photoreceiver 15 present in the same sector, then the decoder 30 decides on the circuit condition L. If the photoreceiver 19 in the oppositely disposed sector 50 of the light beam selector 11 does not receive a signal from the light source 18 which has been reflected by the control reflector 38 the decoder decides on the circuit state H. The logic 34 circuit for the motor control 36 then gives the signal for right hand running of the positioning motor 41. If the two photoreceivers 15 and 19 are energised then the two decoders 30 and 31 both decide on the circuit state L and the logic circuitry 34 switches off the positioning motor 41.

As FIG. 1 shows the light sources and photoreceivers, which are in each case arranged in opposite sectors of the light beam selector 11 form, together with the components which follow them, a common circuit unit which controls in each case one of the two logic circuits 34 and 35 associated with the two control motors 41 and 42.

The signals recorded from the photoreceivers 15, 17, 19, 20 are thus passed as control signals to the control circuit 40 shown in FIG. 4. If the control reflector 38 is approximately at the center of the field of light 45 the control circuit 40 receives signals from the light beam selector 11 illustrated in FIGS. 1, 2 and 3 such that the positioning motor 41 which pivots the lamp reflector 55 about the axis 43 and the positioning motor 42 which pivots the lamp reflector 55 about the axis 44 receive the current value O and the lamp reflector 55 and thus also the field of light will remain in the instaneous position. If the control reflector 38 is now withdrawn sideways from the control field 39 and held at the position desired by the operator then the direction of movement of the control reflector 38 will at once be appropriately registered in the light beam selector 11. The positioning motors 41 and 42 will each be switched on and off by the control circuit 40 so that the lamp reflector 55 moves about its axes 43, 44, depending on the requirements, until the control reflector 38 once again lies in the center of the control field 39, or the field of light 45 which moves therewith, and until the light beam selector 11 receives signals from the control reflector 38 by reflected infrared beams such that, on passing the signals on to the control circuit 40, the drive motors are switched off.

The positioning motor 41 thus obtains from the control circuit 40 shown in FIG. 4 a current for the respectively required direction of rotation and then pivots the lamp reflector 55 about the axis 43 until the beams leaving the light source 18 impinge on the control reflector 38 and are reflected back to the photoreceiver 19. The control circuit 40 now receives a signal from both photoreceivers 15 and 19 and switches the positioning motor 41 off. During the above described course of movement it is also possible, from a particular angular adjustment of the lamp reflector 55 onwards, for the beams transmitted from the light source 20 to fall on the control reflector 38 and be reflected back to the photoreceiver 21. From this moment the positioning motor 42 also receives current from the control circuit 40 for the given direction of rotation and rotates the lamp reflector 55 about the axis 44 until the beams from the light source 16 also fall on the control reflector 38 and can be reflected back to the photoreceiver 17. If the two photoreceivers 17 and 21 are now likewise energised the control circuit 40 switches the positioning motor 42 off. The field of light 45 is then aligned and the control reflector 38 lies at its center.

In this manner the lamp reflector 55 automatically follows the control reflector 38 on lateral displacement of the control reflector 38 so that the operator can automatically regulate the operating theatre lamp simply by arranging the control reflector 38 at the position where he desires the light beam 12.

The decoders 30, 31, 32, 33 can also be termed threshold circuits provided with filters, with the respective thresholds deciding whether the associated photoreceiver 15, 17, 19, 21 receives a sufficient quantity of light or not. The logic circuits 34, 35 then transmit a drive rotation signal for the positioning motors(41 and 42 respectively)when only one of the thresholds in the associated pair of detectors(30, 31 and 32, 33 respectively), is exceeded. The direction of rotation of the positioning motors 41, 42 depends on which photoreceiver of the associated pair 15, 19 or 17, 21 receives light and which does not.

The requirements placed on the light beam selector 11 are such that even a very small displacement of the control reflector 38 relative to the control field 39 should result in only one of the associated diametrically opposite disposed pairs of photoreceivers(15, 19 and 17, 21 respectively), receiving a sufficient quantity of light that the aforementioned threshold is exceeded, the other photoreceiver of the respective pair should however not receive a sufficient quantity of light that the associated threshold is exceeded. The speed of response of the control circuit depends on how quickly one of the photoreceivers no longer receives a sufficient quantity of light to exceed the associated threshold following displacement of the control reflector 38.

This inherent response time can be exploited to ensure that the lamp remains in the desired position when the surgeon withdraws the retroreflector so that he can commence or continue the operation itself. It is namely possible for the surgeon to withdraw the retroreflector from the illuminated area so rapidly that substantially no adjustment of the lamp occurs.

I claim:

1. An operating theatre lamp which transmits a directed beam of light, which is pivotally arranged about two axes which are substantially perpendicular to one another and to the light beam above the site of an operation and which generates a restricted field of light within the site of the operation,wherein said restricted field of light can be substantially horizontally displaced through pivotal movement of the lamp, characterised in that the operating theatre lamp has a light beam selector (11) which is movable with the lamp, which comprises light sources (14, 16, 18, 20) and light receivers (15, 17, 19, 21), and which concentrates a beam of electromagnetic radiation (46) narrower than said light beam (12) and in a different frequency range into a control field (39) within the field of light (45);in that a control reflector (38) is provided which is displaceable in a horizontal plane within the site of the operation, which is matched to the size of the control field (39) and is likewise smaller than the field of light (45) and which reflects the electromagnetic radiation (46) back on itself, at least in part, to the photoreceivers (15, 17, 19, 21); and in that the light sources (14, 16, 18, 20) and the photoreceivers (15, 17, 19, 21) are so arranged in the light beam selector (11) that, when the control reflector (38) leaves the control field (39), the photoreceivers (15, 17, 19, 21) transmit signals to an electronic control circuit (40) through which positioning motors (41, 42) connected to the control circuit (40) are actuated to pivot the lamp about the two axes in the sense of a follow-up adjustment of the control field (39).

2. Operating theatre lamp in accordance with claim 1, characterized in that the control field (39) is arranged at the center of the field of light (45).

3. An operating theatre lamp in accordance with claim 1, in that the diameter of the control field (39) amounts to from ¼ to ¾, and in particular to approximately ½ of the diameter of the field of light (45).

4. An operating theatre lamp in accordance with claim 1, characterized in that the control reflector (38) is a retro-reflector, in particular a triple prism.

5. An operating theatre lamp in accordance with claim 1, characterized in that the light sources (14, 16, 18, 20) and photoreceivers (15, 17, 19, 21) are distributed pairwise in four sectors (50, 51, 52, 53) the bisectors of which extend substantially parallel to the axes (41, 42); wherein the photoreceivers (17, 21; 15, 19) which are arranged on a bisector receive light which does not fall centrally into the light beam selector (11) with differential intensity and control, via the control circuit (40), the pivoting of the lamp about the axes (44; 43) which are at right angles to the relevant bisectors.

6. An operating theatre lamp in accordance with claim 5, characterized in that the angular selection is obtained by arranging the light sources (14, 16, 18, 20) and photoreceivers (15, 17, 19, 21) at the base (49) of a tube (47) which is open at the bottom and which has two flat interior walls (48) arranged at right angles to one another in correspondence with the sectors (50, 51, 52, 53).

7. An operating theatre lamp in accordance with claim 1, characterized in that each light source (14, 16, 18, 20) is operated with a different pulse frequency and in that the associated photoreceivers (15, 17, 19, 21) are tuned by means of electric filters provided within the control circuit (40) to the pulse frequency of the associated light source.

8. An operating theatre lamp in accordance with claim 1, characterized in that the electromagnetic radiation (46) is an infrared radiation.

9. An operating theatre lamp in accordance with claim 1, characterized in that respective diametrically oppositely disposed photoreceivers (15, 19; 17, 21) are connected in pairs, each via a respective threshold circuit (30, 31;, 32, 33), to a logic circuit (35; 35), which in each case controls one of the positioning motors (41; 42) and transmit a drive rotating signal for a certain direction, depending on whether one of the thresholds in the associated threshold circuits (30, 31; 32, 33) has been exceeded.

* * * * *

UNITED STATES PATENT AND TRADEMARK OFFICE
CERTIFICATE OF CORRECTION

PATENT NO. : 4,578,575

DATED : March 25, 1986

INVENTOR(S) : Eberhard Roos

It is certified that error appears in the above-identified patent and that said Letters Patent is hereby corrected as shown below:

On the title page assignee should read:

-- (73) Assignee: Delma, elektro- und medizinishche Apparatebau Gesellschaft mbH --.

Signed and Sealed this

Sixth Day of January, 1987

Attest:

DONALD J. QUIGG

Attesting Officer

Commissioner of Patents and Trademarks